(12) United States Patent
Marino et al.

(10) Patent No.: US 8,460,308 B2
(45) Date of Patent: Jun. 11, 2013

(54) INSERTION AND REDUCTION TOOL FOR PEDICLE SCREW ASSEMBLY

(75) Inventors: James F. Marino, La Jolla, CA (US); Jamil Elbanna, San Diego, CA (US)

(73) Assignee: Trinity Orthopedics, LLC., San Diego, CA (US)

(*) Notice: Subject to any disclaimer, the term of this patent is extended or adjusted under 35 U.S.C. 154(b) by 778 days.

(21) Appl. No.: 12/579,294

(22) Filed: Oct. 14, 2009

(65) Prior Publication Data
US 2010/0137875 A1 Jun. 3, 2010

Related U.S. Application Data

(60) Provisional application No. 61/105,361, filed on Oct. 14, 2008.

(51) Int. Cl.
*A61B 17/58* (2006.01)
*A61B 17/88* (2006.01)

(52) U.S. Cl.
USPC .......................................... 606/104; 606/279

(58) Field of Classification Search
USPC ........................... 606/104, 264–267, 270, 279
See application file for complete search history.

(56) References Cited

U.S. PATENT DOCUMENTS

| | | | |
|---|---|---|---|
| 5,318,589 A | 6/1994 | Lichtman | |
| 5,499,983 A | 3/1996 | Hughes | |
| 6,440,133 B1 | 8/2002 | Beale et al. | |
| 6,485,494 B1 | 11/2002 | Haider | |
| 6,648,888 B1 | 11/2003 | Shluzas et al. | |
| 6,660,006 B2 | 12/2003 | Markworth et al. | |
| 7,160,300 B2 | 1/2007 | Jackson | |
| 7,377,923 B2 | 5/2008 | Purcell et al. | |
| 8,096,996 B2 * | 1/2012 | Gutierrez et al. | 606/86 A |

(Continued)

FOREIGN PATENT DOCUMENTS

| | | |
|---|---|---|
| WO | 2006/116606 | 11/2006 |
| WO | 2010/045383 | 4/2010 |

OTHER PUBLICATIONS

R. Zeller, J.Dubousset, The Technique of the New CD Horizon: How We Operate on Adolescent Idiopathic Scoliosis, Apr. 7, 2011, Maitrise Orthopedique Le journal orthopedique sur le web, http://www.maitrise-orthop.com/viewPage_us.do?id=119.

*Primary Examiner* — Nicholas Woodall
(74) *Attorney, Agent, or Firm* — Fred C. Hernandez; Mintz Levin Cohn Ferris Glovsky and Popeo, P.C.

(57) ABSTRACT

Disclosed are devices, methods and systems for manipulating a pedicle screw assembly and for inserting and reducing a rod relative to the pedicle screw assembly. The system can include a cannula assembly having a reduction cannula with an internal bore extending between a proximal region and a distal region and an insertion cannula co-axially positioned within the internal bore of the reduction cannula. The insertion cannula includes a pair of opposed prongs extending distally from a distal region of the insertion cannula, wherein each prong is interposed between a pair of flexible projecting elements. The pair of opposed prongs of the insertion cannula and the distal region of the reduction cannula are aligned to collectively define an opening that is sized and shaped for receiving a spinal rod. The device also can include an annular collar mounted on the proximal region of the reduction cannula and rotatably coupled to a proximal region of the insertion cannula. The cannula assembly can also be a pivoting cannula assembly.

11 Claims, 17 Drawing Sheets

U.S. PATENT DOCUMENTS

| | | |
|---|---|---|
| 2002/0035366 A1 | 3/2002 | Walder |
| 2003/0199872 A1 | 10/2003 | Markworth et al. |
| 2005/0192579 A1* | 9/2005 | Jackson .......................... 606/72 |
| 2005/0228392 A1 | 10/2005 | Keyer et al. |
| 2006/0069391 A1 | 3/2006 | Jackson |
| 2006/0074418 A1 | 4/2006 | Jackson |
| 2006/0111713 A1* | 5/2006 | Jackson .......................... 606/61 |
| 2006/0293690 A1 | 12/2006 | Abdelgany |
| 2007/0233155 A1* | 10/2007 | Lovell .......................... 606/104 |
| 2008/0077138 A1 | 3/2008 | Cohen et al. |
| 2008/0234759 A1 | 9/2008 | Marino |

* cited by examiner

INSERTION AND REDUCTION TOOL FOR PEDICLE SCREW ASSEMBLY

RELATED APPLICATIONS

This application claims the benefit of priority under 35 U.S.C. §119(e) of U.S. Provisional Application Ser. No. 61/105,361, filed Oct. 14, 2008, entitled "INSERTION AND REDUCTION TOOL FOR PEDICLE SCREW ASSEMBLY". The subject matter of the above-noted application is incorporated by reference in its entirety by reference thereto.

This application is also related to U.S. application Ser. No. 11/916,277, filed Apr. 27, 2006, entitled "Mono-Planar Pedicle Screw Method, System and Kit" which is a national stage application of and claims the benefit of PCT/US2006/016042 filed on Apr. 27, 2006, which claims the benefit of U.S. Provisional Patent Application No. 60/675,742, filed Apr. 27, 2005, and entitled "Uni-axial Pedicle Screw Construct with Set Screw and Percutaneous Rod Linkage Features Method, System, and Kit". The subject matter of these applications are incorporated by reference in its entirety by reference thereto.

BACKGROUND

Spinal fixation devices are used in orthopedic surgery to align and/or fix a desired relationship between adjacent vertebral bodies. Pedicle screw assemblies, for example, typically include a screw having a threaded shank that is adapted to be threaded into a vertebra, and a head portion having a rod-receiving element, usually in the form of a U-shaped slot formed in the head. A set-screw, plug, or similar type of fastening mechanism, is used to lock a fixation rod seated in the rod-receiving head of the pedicle screw to securely interconnect each screw and the fixation rod.

Rod reduction is often necessary to position and hold the rod against the seat of the rod-receiver. Rod persuader instruments that are used to perform rod reduction must apply sufficient force to position the rod in the receiver of the pedicle screw. Some rod persuader instruments are actuated by articulating handles that extend laterally from the main shaft of the instrument. This can add undesired weight to the instrument and create a visual obstruction over the implant site. Other rod persuader instruments require constant force to be applied manually on the actuator to hold the rod in the seated position while the set screw is manipulated. This limits the use of one hand when the set screw is being inserted and tightened into place. In addition, it can be difficult to align and seat the rod into the rod-receiver of adjacent fixation devices due to the positioning and rigidity of the vertebra into which the fixation device is mounted.

Accordingly, there is a need for improved rod reduction devices and methods for seating a spinal rod, or other spinal fixation element, into one or more spinal implants or fasteners.

SUMMARY

Disclosed are devices and methods for the treatment of the spine. In particular, disclosed are devices and methods for the insertion and reduction of connecting rods into fixation device assemblies for the treatment of the spine.

In one aspect, there is disclosed a spinal rod insertion and reduction device including a cannula assembly having a reduction cannula with an internal bore extending between a proximal region and a distal region and an insertion cannula co-axially positioned within the internal bore of the reduction cannula. The insertion cannula comprises a pair of opposed prongs and at least one flexible projecting element extending distally from a distal region of the insertion cannula. The pair of opposed prongs of the insertion cannula and the distal region of the reduction cannula are aligned to collectively define an opening that is sized and shaped for receiving a spinal rod.

In an embodiment, the device can include an annular collar mounted on the proximal region of the reduction cannula and rotatably coupled to a proximal region of the insertion cannula. Rotation of the collar can impart relative linear movement between the insertion cannula and reduction cannula along a long axis of the cannula assembly. Relative linear movement between the insertion cannula and reduction cannula can provide gradual and forceful translation of the reduction cannula distally along the long axis of the cannula assembly. The collar can be mounted to the reduction cannula via a slip plane that permits the collar to rotate about the reduction cannula. The collar can also have internal threads that rotatably couple to threads on the proximal region of the insertion cannula. The opposed prongs can be configured to insert into a pair of longitudinal channels on an external surface of a fixation device receiver element. The flexible projecting element can be radially displaceable. The projecting element can include a flange on an internal surface that engages a slot intersecting the longitudinal channel upon insertion of the prong into the channel. The reduction cannula can stabilize the opposed prongs and confine the projecting element to prevent dissociation of the insertion cannula from the receiver element. The dimensions of the cannula assembly along a first axis can be less than dimensions of the cannula assembly along a second axis perpendicular to the first axis.

The device can further include a disengagement tool having an actuation handle, a cannula assembly coupler configured to couple the disengagement tool to the cannula assembly, and an elongate arm comprising a distal control element. The elongate arm can insert through an internal bore of the insertion cannula and the cannula assembly coupled can be coupled at a proximal end to the cannula assembly. The distal control element can include an opening configured to receive and hold a compression nut. The control element can include one or more displacing elements that sequentially splay the projecting element radially outward and push downward on an upper surface of the compression nut while simultaneously engaging the internal bore of the insertion cannula to disengage the insertion cannula from the receiver element. The disengagement tool can apply negligible net force to the receiver element during disengagement of the insertion cannula from the fixation device receiver element. The reduction cannula can have one or more visual markers on an outer surface. The one or more visual markers can be a channel, a slot and indicia and the like. The marker can include an external longitudinal trough through which a distal tapered tip of the spinal rod can be translated distally during insertion through the opening. The distal region of the reduction cannula can have a vaulted leading edge.

In another aspect, there is disclosed a spinal rod insertion and reduction device including a reduction cannula having an internal bore extending between a proximal region and a distal region; and an insertion cannula co-axially positioned within the internal bore of the reduction cannula and comprising a joint having a pivot axis that is transverse to a long axis of the insertion cannula. The joint couples together a proximal, articulating element to a distal cannula element such that the proximal, articulating element pivots about the pivot axis along a single plane.

The joint can be a pinned joint. The pinned joint can include one or more hinge pins extending through a first pair of opposed apertures near a distal region of the proximal, articulating element and a second pair of opposed apertures near a proximal region of the distal cannula element, wherein the first and second pairs of opposed apertures are aligned. The proximal, articulating element can pivot between about 30 degrees caudal and 30 degrees cephalad from the long axis of the insertion cannula. The distal cannula element can include a pair of opposed prongs and at least one flexible projecting element extending distally from the distal cannula element. The pair of opposed prongs of the insertion cannula and the distal region of the reduction cannula can be aligned to collectively define an opening that is sized and shaped for receiving a spinal rod. The opposed prongs can be configured to insert into a pair of longitudinal channels on an external surface of a fixation device receiver element. The flexible projecting element can be radially displaceable. The projecting element can include a flange on an internal surface that engages a slot intersecting the longitudinal channel upon insertion of the prong into the channel. The device can also include an annular collar mounted on the proximal region of the reduction cannula. The annular collar can be rotatably coupled to a proximal region of the insertion cannula. Rotation of the collar can impart relative linear movement between the insertion cannula and reduction cannula along the long axis of the insertion cannula. Relative linear movement between the insertion cannula and reduction cannula can provide gradual and forceful translation of the reduction cannula distally along the long axis of the insertion cannula. The collar can be mounted to the reduction cannula via a slip plane that permits the collar to rotate about the reduction cannula. The collar can have internal threads that rotatably couple to threads on the proximal, articulating element.

Also disclosed are methods of using the devices described herein. In an embodiment, disclosed is a method of inserting a reducing a spinal rod into a fixation device assembly that includes providing a fixation device assembly having a fixation device engaged with a bone and a rod receiver element having an outer surface comprising a pair of opposed longitudinal channels, each channel intersected cross-wise by a slot. The method also includes coupling a cannula assembly to the receiver element, the cannula assembly including a reduction cannula having an internal bore extending between a proximal region and a distal region; and an insertion cannula co-axially positioned within the internal bore of the reduction cannula. The insertion cannula includes a pair of opposed prongs and at least one flexible projecting element extending distally from a distal region of the insertion cannula. The pair of opposed prongs of the insertion cannula and the distal region of the reduction cannula are aligned to collectively define an opening that is sized and shaped for receiving a connecting rod. The method also includes sliding the prongs of the insertion cannula into the longitudinal channels of the receiver element. The flexible projecting element temporarily splays outward and subsequently recoils into engagement with the slots intersecting the longitudinal channels as the prongs slide into the channels. The method also includes inserting the connecting rod into the opening and moving the reduction cannula distally toward the fixation device while the insertion cannula maintains the fixation device assembly in a desired position. Inserting the connecting rod can include translating a distal tapered tip of the connecting rod distally within a longitudinal trough positioned along an outer surface of the reduction cannula.

More details of the devices, methods and systems for spinal rod insertion and reduction into a pedicle screw assembly are set forth in the accompanying drawings and the description below. Other features and advantages will be apparent from the description and drawings, and from the claims.

BRIEF DESCRIPTION OF THE DRAWINGS

These and other aspects will now be described in detail with reference to the following drawings. Generally speaking the figures are not to scale in absolute terms or comparatively but are intended to be illustrative of claimed features. Also, relative placement of features and elements may be modified for the purpose of illustrative clarity.

DETAILED DESCRIPTION

Disclosed are devices, methods and systems for manipulating a pedicle screw assembly and for inserting and reducing a rod relative to the pedicle screw assembly. The system can include a cannula assembly that can be used to insert and reduce the rod. The assembly has several functions. For example, the cannula assembly can attach to a receiver element of the pedicle screw assembly for open and percutaneous pedicle screw placement and manipulation. The cannula assembly can have an enlarged channel or aperture for connecting rod insertion, and can be used to reduce the connecting rod to the receiver element immediately prior to the application of the set screw.

Figure 1:
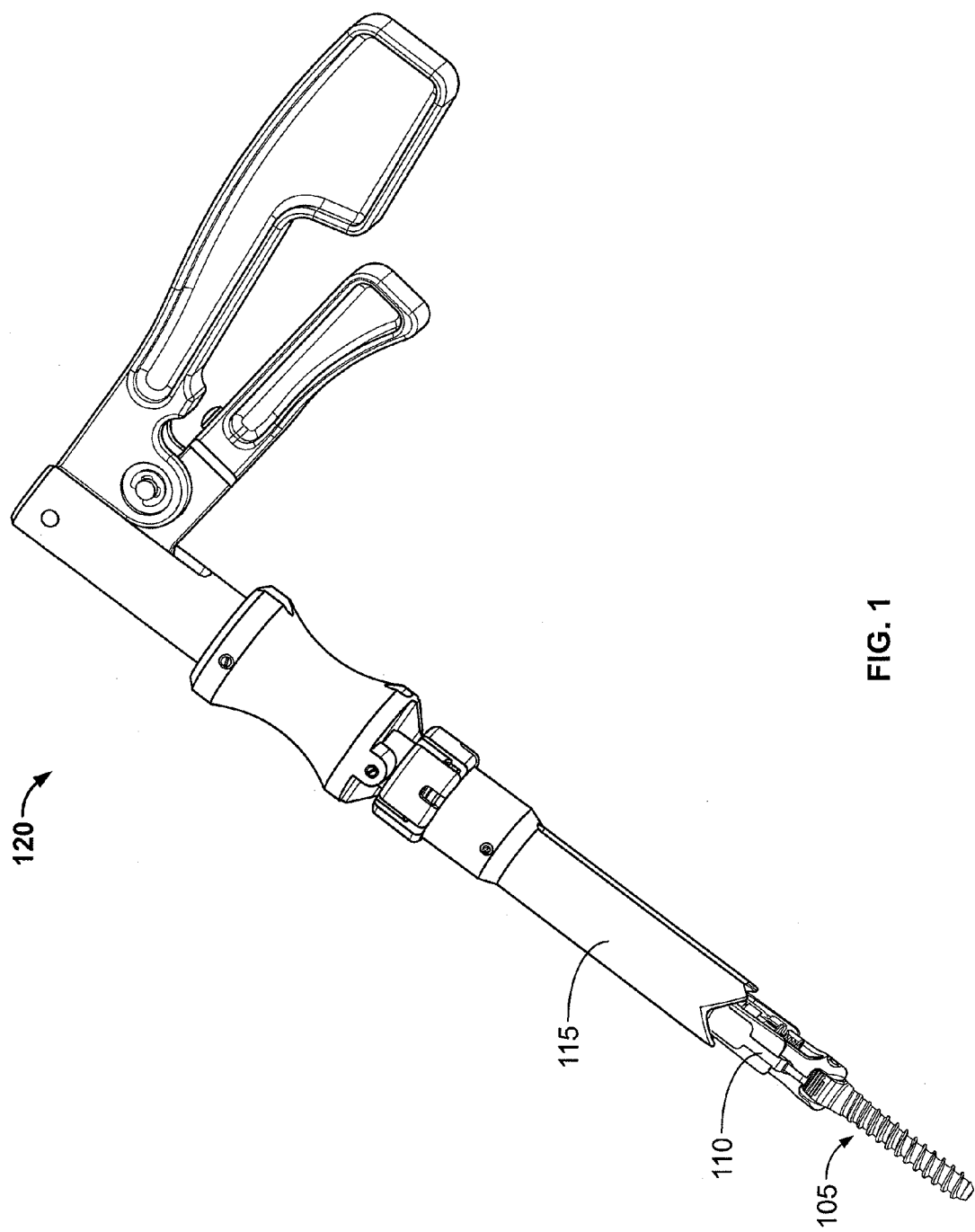
FIG. 1 shows a perspective view of an insertion and reduction system.

FIG. 1 shows a perspective view of an insertion and reduction system for bone screws. The system can attach to a bone screw assembly, such as a pedicle screw assembly 105. The system can be used for open and percutaneous placement and manipulation of a pedicle screw assembly 105. In an exemplary embodiment, the system includes a cannula assembly having an insertion cannula 110 and a reduction cannula 115. The system further can include a disengagement tool 120 that interfaces with the insertion cannula 110 and reduction cannula 115 (see FIG. 6). In an assembled state, the insertion cannula 110 can be inserted within and its internal bore 417 co-axially aligned with an internal bore 117 of the reduction cannula 115.

Figure 2A:
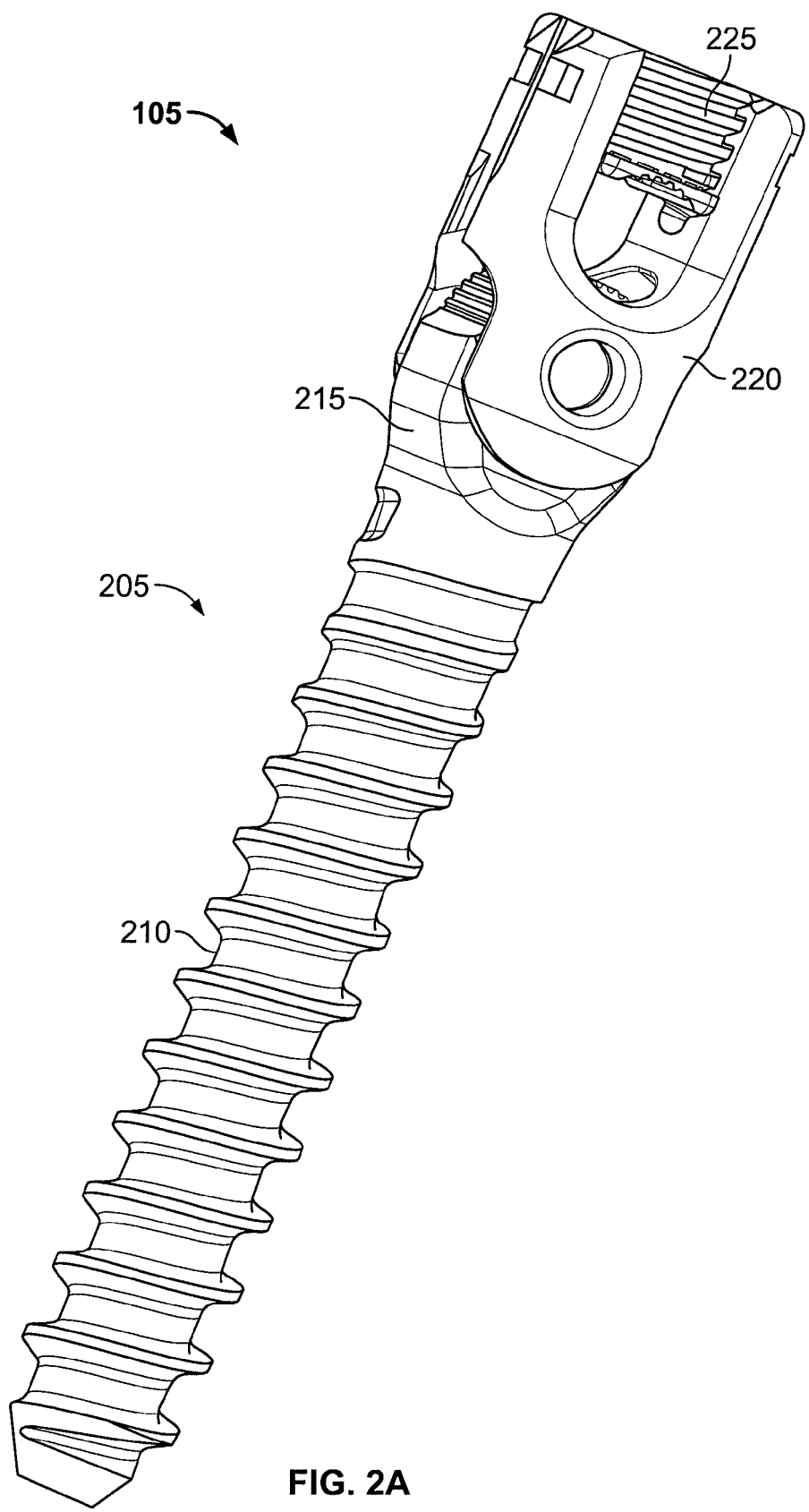
FIG. 2A shows a perspective view of an exemplary pedicle screw assembly.

FIG. 2A shows a perspective view of the pedicle screw assembly 105. The assembly 105 can include a fixation component 205 (such as a bone screw) with a threaded shank 210 that inserts into bone, and a head 215 that couples to a receiver 220. In the illustrated embodiment, the head 215 is rotatably coupled to the receiver 220. The pedicle screw assembly 105 can be a mono-planar assembly such that the fixation component 205 can rotate only within a single plane relative to the receiver 220. It should be appreciated that the pedicle screw assembly 105 can also be a mono-axial or a poly-axial assembly.

Figure 2B:
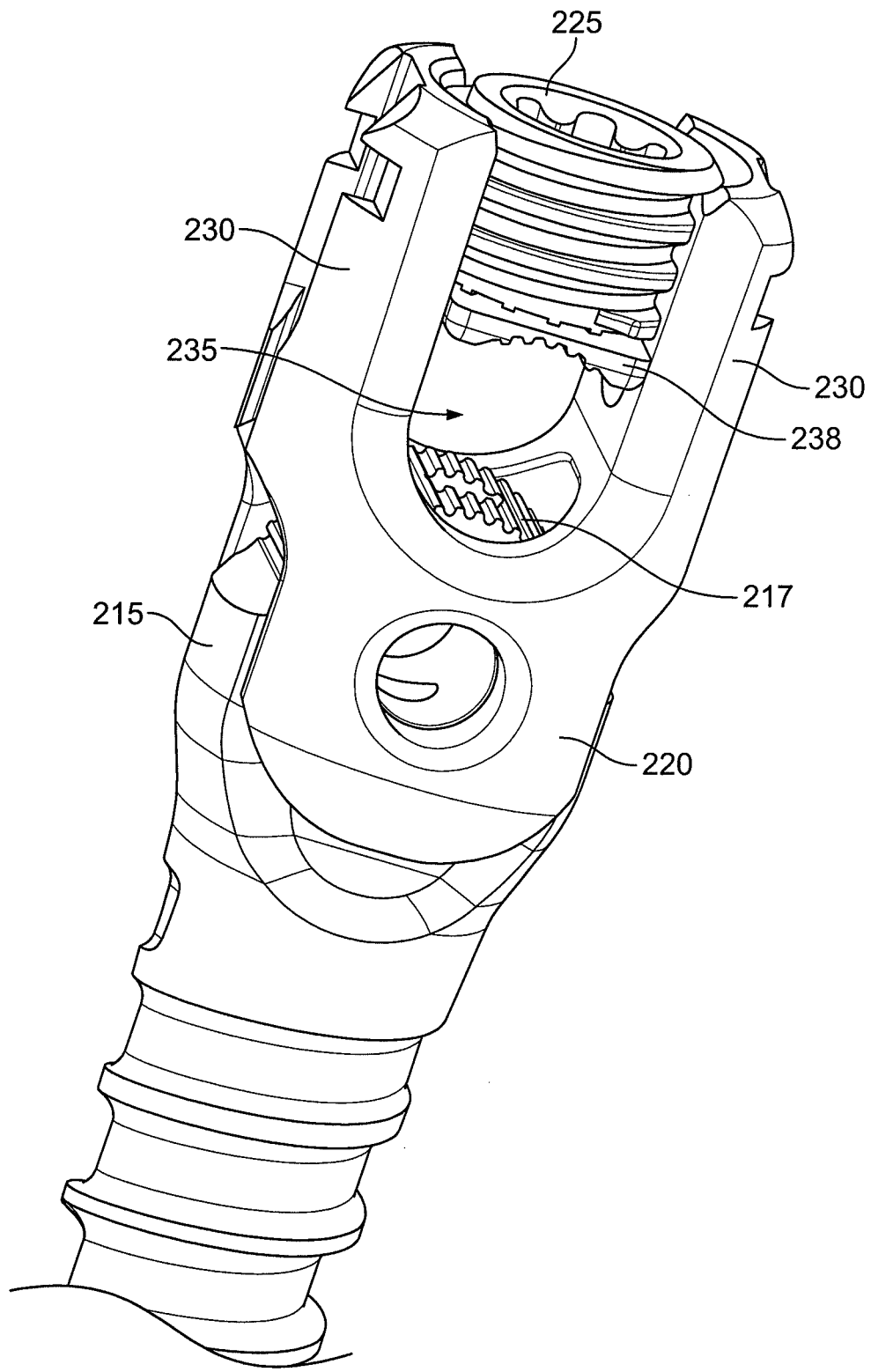
FIG. 2B shows an enlarged view of a receiver and a head of the fixation component of the pedicle screw assembly.

FIG. 2B shows an enlarged view of the receiver 220 and the head 215 of the fixation component 205. The receiver 220 can include a pair of upwardly-extending prongs 230 that define an opening 235 therebetween that can receive a compression nut 225. The compression nut 225 can couple to the interior of the prongs 230 via a threaded connection. This permits the compression nut 225 to be threaded downward (i.e., distally) into the opening 235. A rod (not shown) can be positioned in the opening 235 such that the rod contacts the head 215. As the compression nut 225 is threaded downward, it provides a compressive force onto the rod and onto the head 215. In this manner, the rod, head 215 and receiver 220 can be locked or immobilized relative to one another.

In an embodiment, the fixation component head 215 has a mating feature that facilitates a secure mating between the head 215 and the rod. The mating feature can be for example, scallops or splines 217 that extend along the head 215, as shown in FIG. 2B. The splines 217 can interdigitate with complementary mating features, such as splines, on the rod. The compression nut 225 can include a bottom washer 238 rotatably coupled to the compression nut 225. The bottom washer 238 has a bottom surface that contacts the rod. The bottom surface of the washer 238 can also have a mating feature, such as splines, that mate with the corresponding mating feature(s) on the rod (such as in an interdigitating fashion).

Figure 2C:
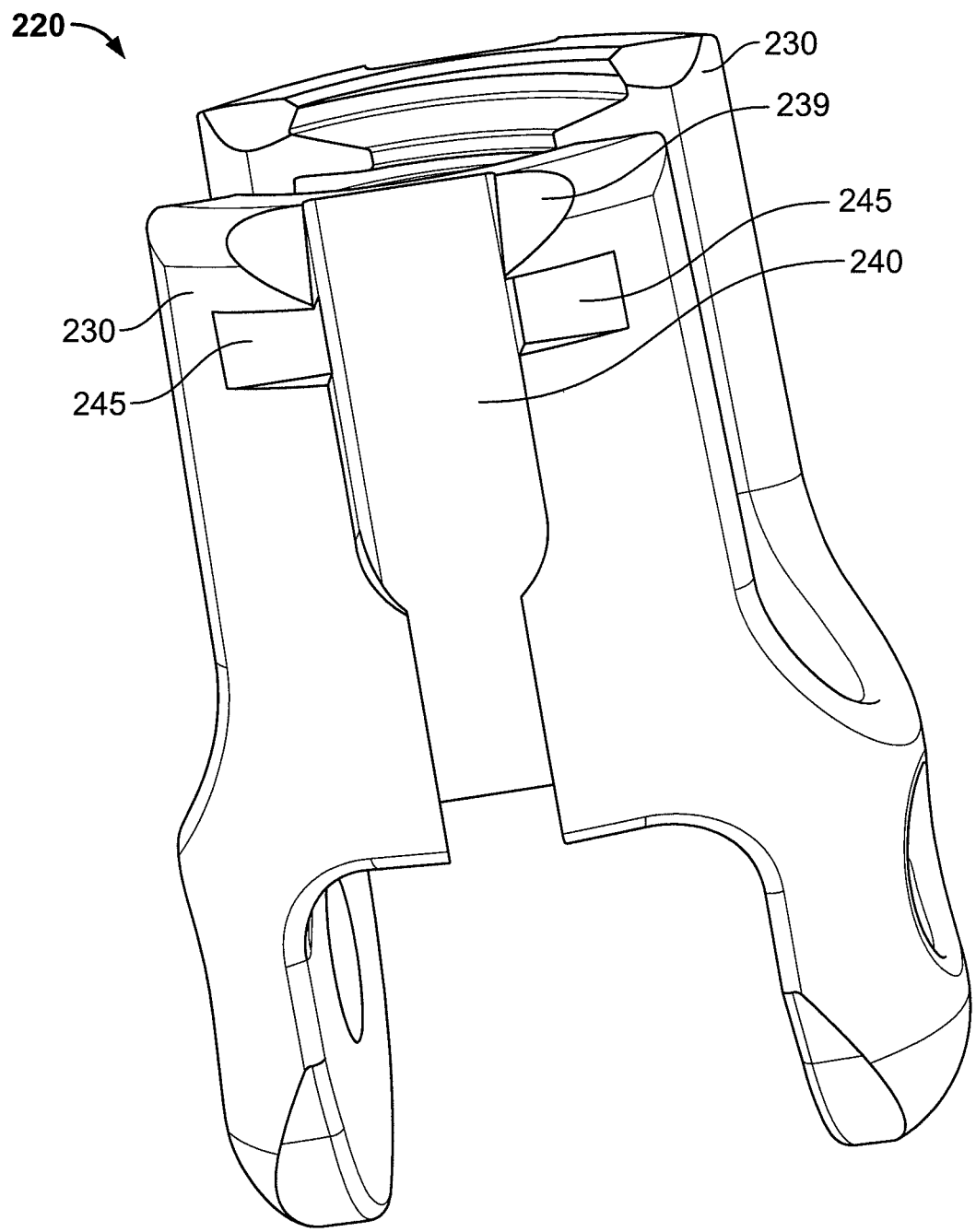
FIG. 2C shows an enlarged view of the receiver looking toward one of the prongs of the receiver.
Figure 2D:
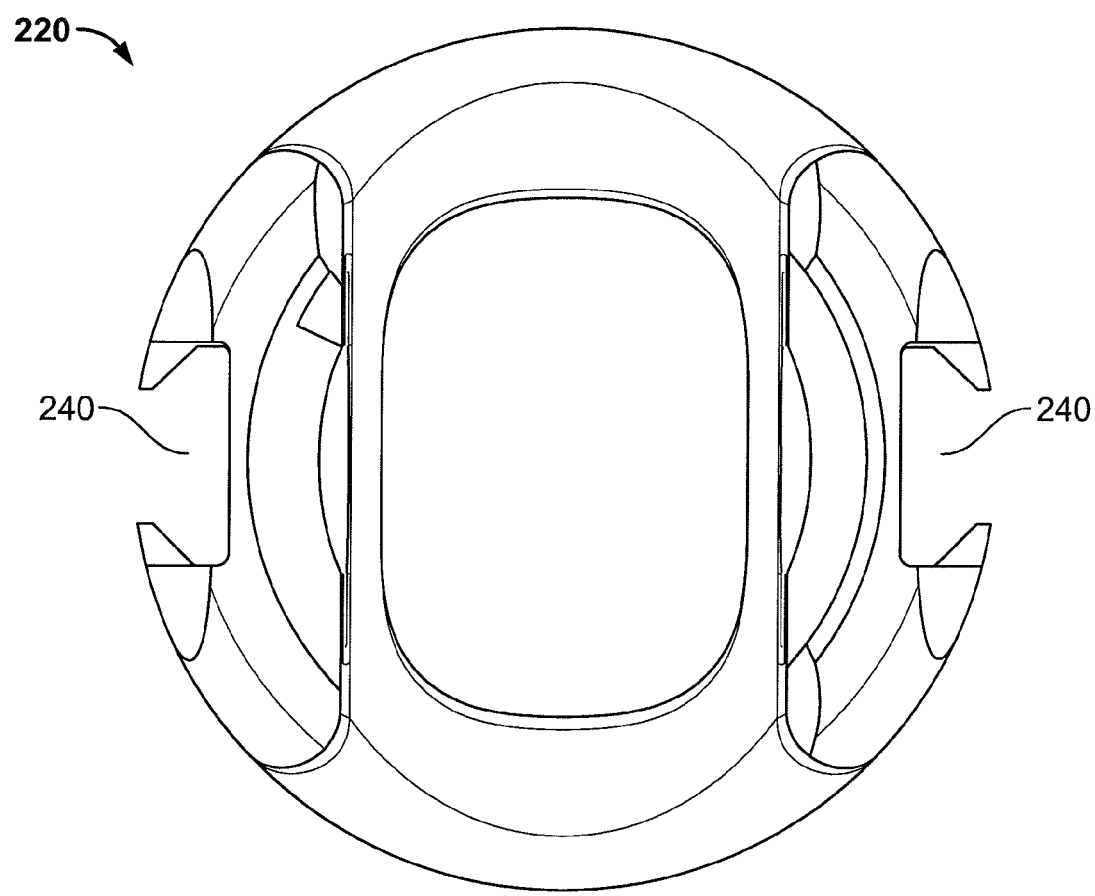
FIG. 2D shows a top view of the receiver.

The receiver 220 can include one or more mating features that provide for a secure and strong coupling between the insertion cannula 110 and the pedicle screw assembly 105. This is described in more detail with reference to FIG. 2C, which shows an enlarged view of the receiver 220 looking toward one of the prongs 230 of the receiver 220. The remaining components of the pedicle screw assembly 105 are not shown in FIG. 2C for clarity of illustration. The outer aspect of each prong 230 can include a channel 240 that extends along a distal-proximal direction from a chamfered proximal edge 239 of the receiver 220. The channel 240 is sized and shaped to receive a prong 410 (FIG. 4B) of complementary size and shape on the insertion cannula 110. In this regard, the channel 240 and prong 410 have complementary dove-tail configurations. As shown in the top view of FIG. 2D, the channels 240 can extend into the receiver 220 such that an overhang/undercut arrangement is achieved. This permits a dove-tail mating arrangement between the channels 240 and complementary prongs 410 of the insertion cannula 110, as described below.

With reference again to FIG. 2C, each prong 230 can include a slot 245 that intersects cross-wise with the channel 240. Each slot 245 can mate with a complementary projecting element 415 (FIG. 4B) on the insertion cannula 220, as described below.

Figure 3A:
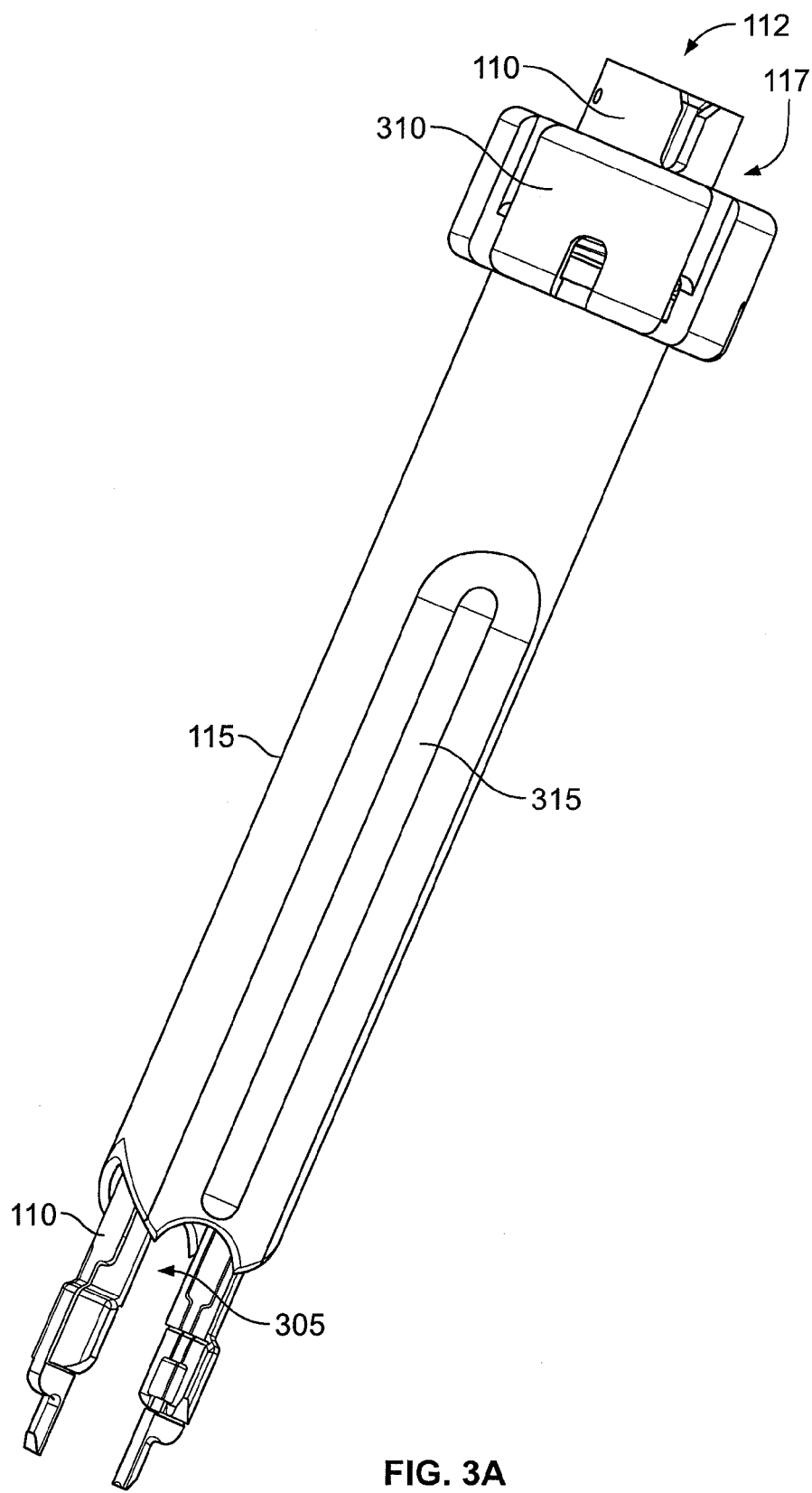
FIG. 3A shows a perspective view of a cannula assembly that includes an insertion cannula and a reduction cannula.

FIG. 3A shows a perspective view of a cannula assembly that includes the insertion cannula 110 and the reduction cannula 115, which is coaxially positioned over the insertion cannula 110. A collar 310 can be rotatably mounted on a proximal end of the reduction cannula 115, for example by a slip plane that permits the collar 310 to rotate about the reduction cannula 115. The collar 310 can have internal threads (not shown) that interface with corresponding threads 405 on the proximal region of the insertion cannula 110, as described more fully below. The collar 310 can be rotated to achieve relative linear movement between the insertion cannula 110 and reduction cannula 115 along the co-axial long axes of the cannulae.

The cannulae 110, 115 collectively define a vaulted opening 305 that can be sized and shaped for receiving a rod. The insertion cannula 110 and/or the reduction cannula 115 can include one or more visual or tactile markers 315, such as slots, troughs, indicia, etc. that assist in proper alignment of the system during use. The markers 315 can be on any of a variety of locations on the cannulae. For example, the markers 315 can be on the proximal aspect of the insertion 110 and reduction 115 cannulae and can be used to, for example, to align instruments relative to the receiver opening 235 for the purpose of set screw 225 washer 238 alignment. The markers 315 can be used to permit secure engagement of a cannulated counter-rotation instrument to stabilize the pedicle screw assembly 105 during final set screw 225 torquing. The markers 315 can be used to provide a visual and/or tactile reference for the purpose of connecting rod placement into the receiver 220. The markers 315 can be used to align the disengagement tool 120 used to separate and remove the insertion cannula 110 from the pedicle screw assembly 105.

Figure 3B:
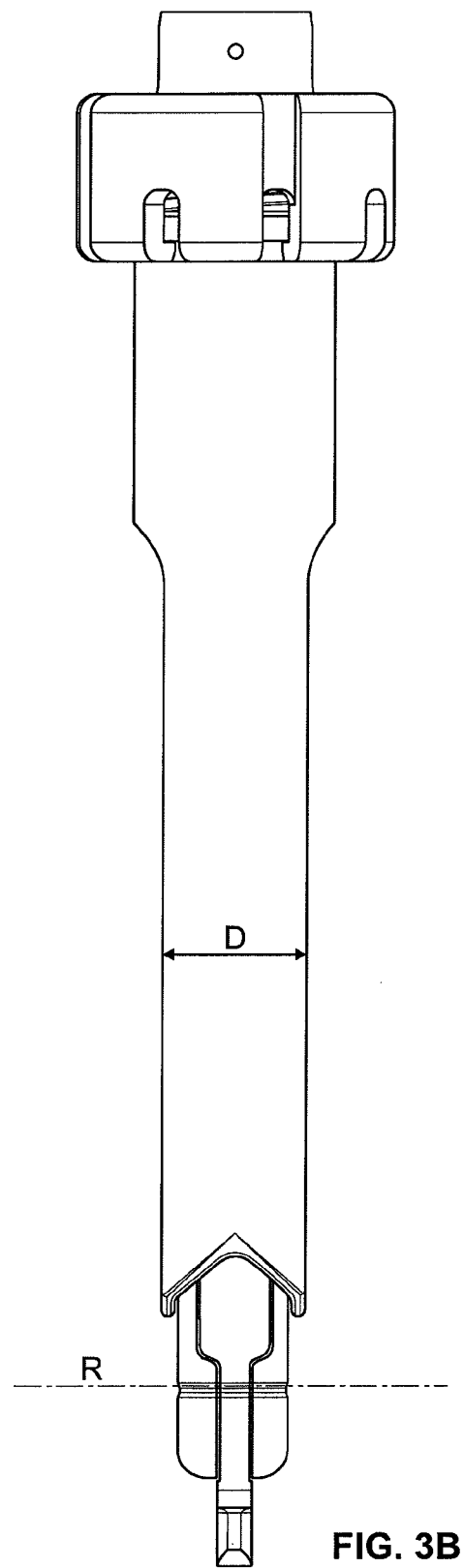
FIG. 3B shows the cannula assembly looking along an axis transverse to the axis R of the connecting rod.

FIG. 3B shows the cannula assembly looking toward an axis transverse to the axis R of a hypothetical connecting rod (such as when a connection rod is properly inserted into an attached pedicle screw assembly 105). The cannulae 110, 115 can have an external and cross-sectional surface geometry that is non-circular distally on the insertion 110 and reduction 115 cannulae. The dimension D of the cannulae 110, 115 along the axis R can be minimized and less than the cannulae 110, 115 dimension associated with an axis perpendicular to the axis R (and generally medial-lateral relative to the patient's anatomy). This geometry can reduce overlap or crowding that can interfere or prevent optimal cannula and receiver element 220 positioning, particularly when the pedicles are in close approximation and when the pedicle axes are convergent, as is frequently the case in the lower lumbar and lumbo-sacral segments (corresponding with narrow disc spaces and lumbar lordosis).

Figure 3C:
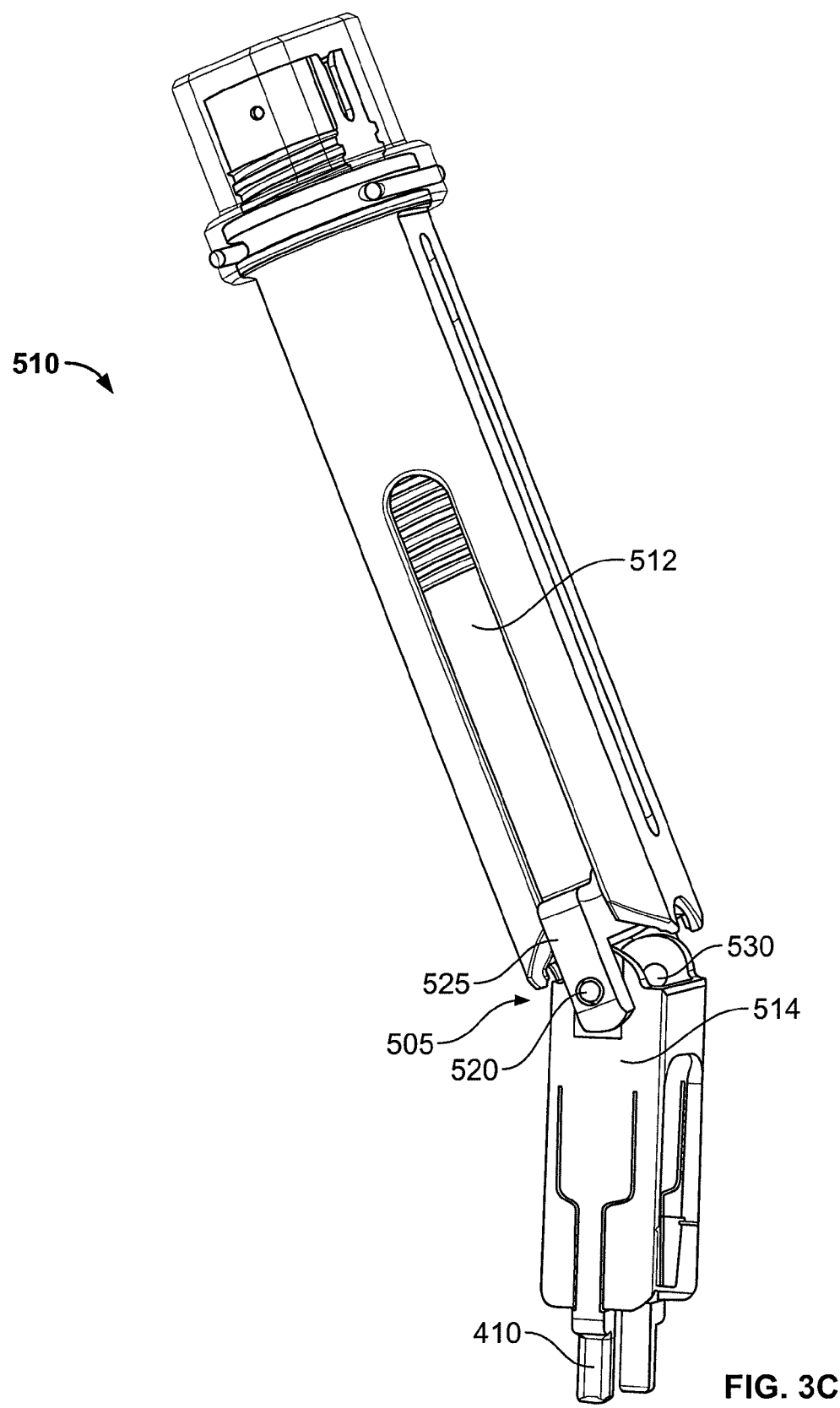
FIG. 3C shows a perspective view of a variation of a cannula assembly that includes an insertion cannula and a reduction cannula.

FIG. 3C shows a perspective view of a variation of an articulating insertion cannula 510. In some instances, more than one cannula assembly can be used simultaneously. An insertion cannula 510 that can be bent or articulated provides for optimal cannulae positioning by reducing overlap or crowding. This allows for two adjacent cannula assemblies to be bent away from each other such that they do not interfere, for example, due to convergence from a typical lordotic curve or when the pedicles are in close approximation.

In an embodiment, the insertion cannula can include an articulating, proximal component 512 and receiver-coupling, distal component 514 that are joined together at a joint 505. The joint 505 can allow for the proximal component 512 to pivot or rotate relative to the distal component 514 coupled to a receiver element 220 along a single plane. The joint 505 can have a pivot axis that is transverse to the long axis of the cannula such that articulation of the proximal component 512 about the pivot axis causes bending of the insertion cannula away from the long axis. The angle or range of articulation can vary. In an embodiment the proximal component 512 can rotate around the joint 505 30 degrees caudal to 30 degrees cephalad from the long axis of the insertion cannula.

In an embodiment, the joint 505 can be a pinned joint or a pivoting hinge joint. The joint 505 can include a pair of pins 515 that extend through apertures 520 in distally-projecting prongs 525 of the proximal component 512. Corresponding apertures 530 in the distal component 514 receive each of the pins 515. When the proximal component 512 and distal component 514 of the insertion cannula are aligned along the longitudinal axis of the cannula assembly, the prongs 525 are aligned with the prongs 410 (see FIG. 3D). When the proximal component 512 and distal component 514 of the insertion cannula 510 are not in alignment and the proximal component 512 is rotated about the pins 520, the prongs 525 are at an angle to prongs 410 (see FIG. 3C). The reduction cannula can include a pair of opposed, elongated slots such that the distal region of the reduction cannula takes on a forked appearance. Prongs 525 of the joint 505 can travel through the slots during, for example, linear translation of the reduction cannula in a distal direction. It should be appreciated that other types of joints are considered. For example, the articulating cannula can incorporate an arcuate channel as an alternative to the pinned hinged joint.

The relative lengths of each of the proximal and distal components can vary and as such the location of the joint 505 along the longitudinal axis of the insertion cannula can vary. In an embodiment, the joint 505 can be located just proximal to each of the distal projecting elements 415 of the distal component 514 near the upper region of the vaulted opening 305.

Figure 3D:
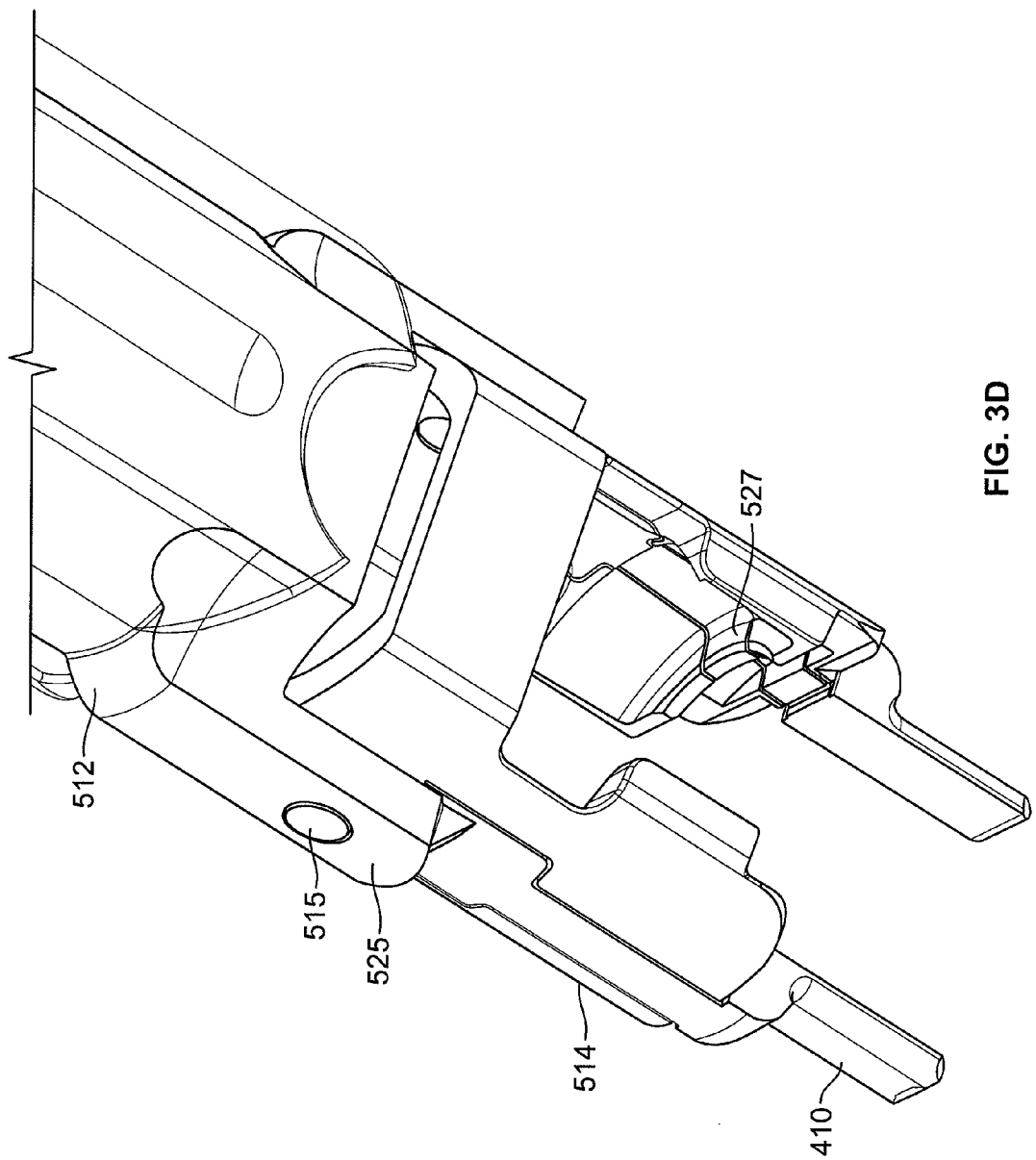
FIG. 3D shows a close up of the cannula assembly of FIG. 3C.

FIG. 3D shows an enlarged view of the joint 505. The cannula assembly can include one or more stabilizing features 527 to prevent misalignment, for example, under unequal loading during reduction of a tightly curved connecting rod. The stabilizing features 527 can minimize the off-axis tilting of the insertion and reduction cannula, for example, when a connecting rod is higher on one side of the receiver element than the other. The stabilizing features 527 on an inner surface of each side of the prongs 410 are loaded in compression opposite the high side of the connecting rod as the reduction cannula is advanced relative to the insertion cannula. This reduces the tilting of the cannulae with respect to the receiver element. It should be understood that any of the features described herein can be used with any of the different embodiment described herein. For example, although the stabilizing feature 527 is described with respect to the articulating cannula it should be appreciated that the cannula need not articulate and the stabilizing feature 527 can be incorporated with any other embodiment described herein.

Figure 4A:
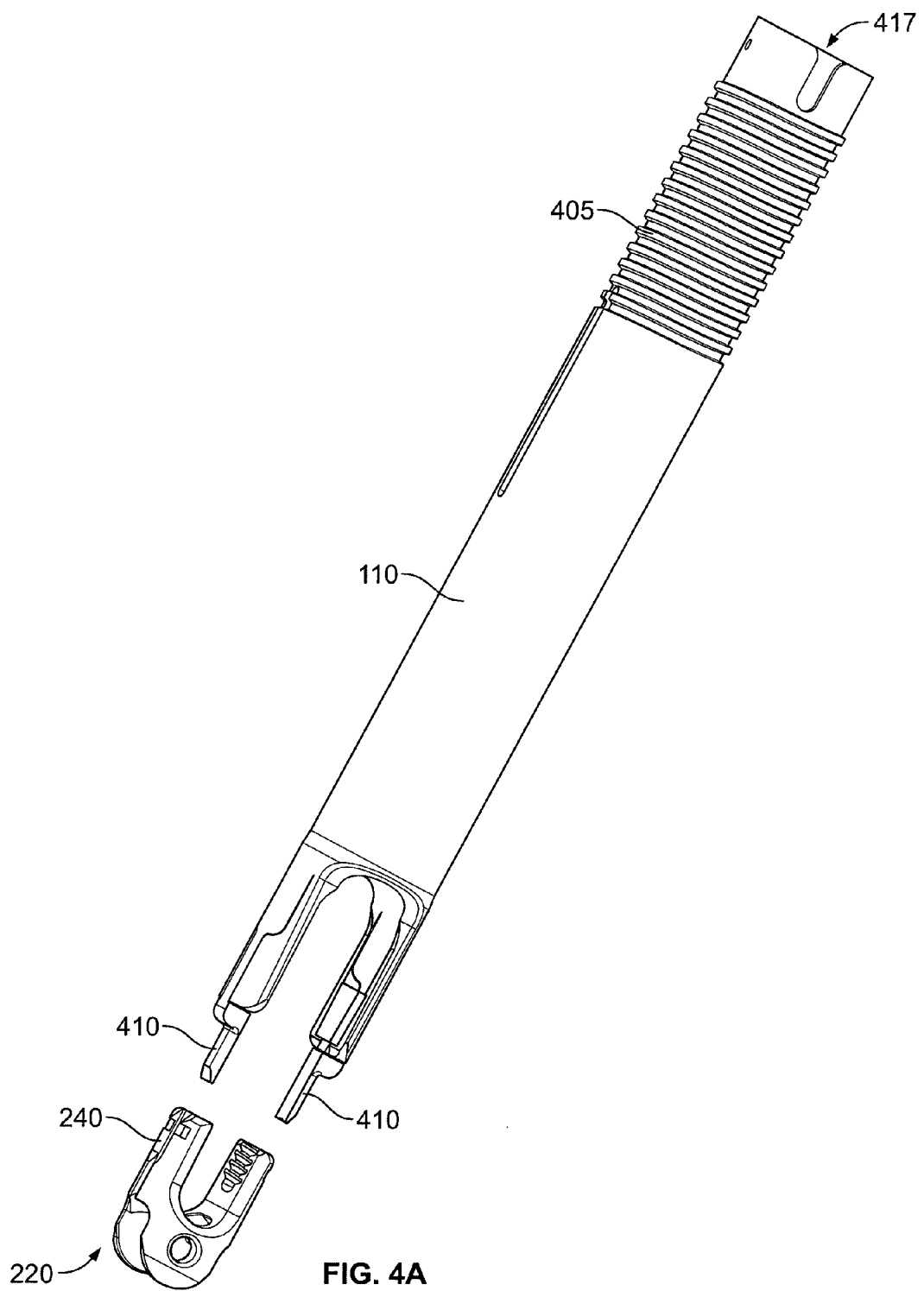
FIG. 4A shows a perspective view of the insertion cannula and the receiver of the pedicle screw assembly.

FIG. 4A shows a perspective view of the insertion cannula 110 and the receiver 220 of the pedicle screw assembly 105. A proximal region of the insertion cannula 110 can include threads 405 that mate with threads on the internal surface of the rotatable collar 310 on the reduction cannula 115. Rotation of the collar 310 allows for gradual and forceful translation of the reduction cannula 115 distally along the common axis of both cannulas. This facilitates reduction of the connecting rod within the receiver element's opening 235, as described below. It should be appreciated that other actuation mechanisms are considered to effect relative linear translation between the insertion 110 and reduction 115 cannulae.

Figure 4B:
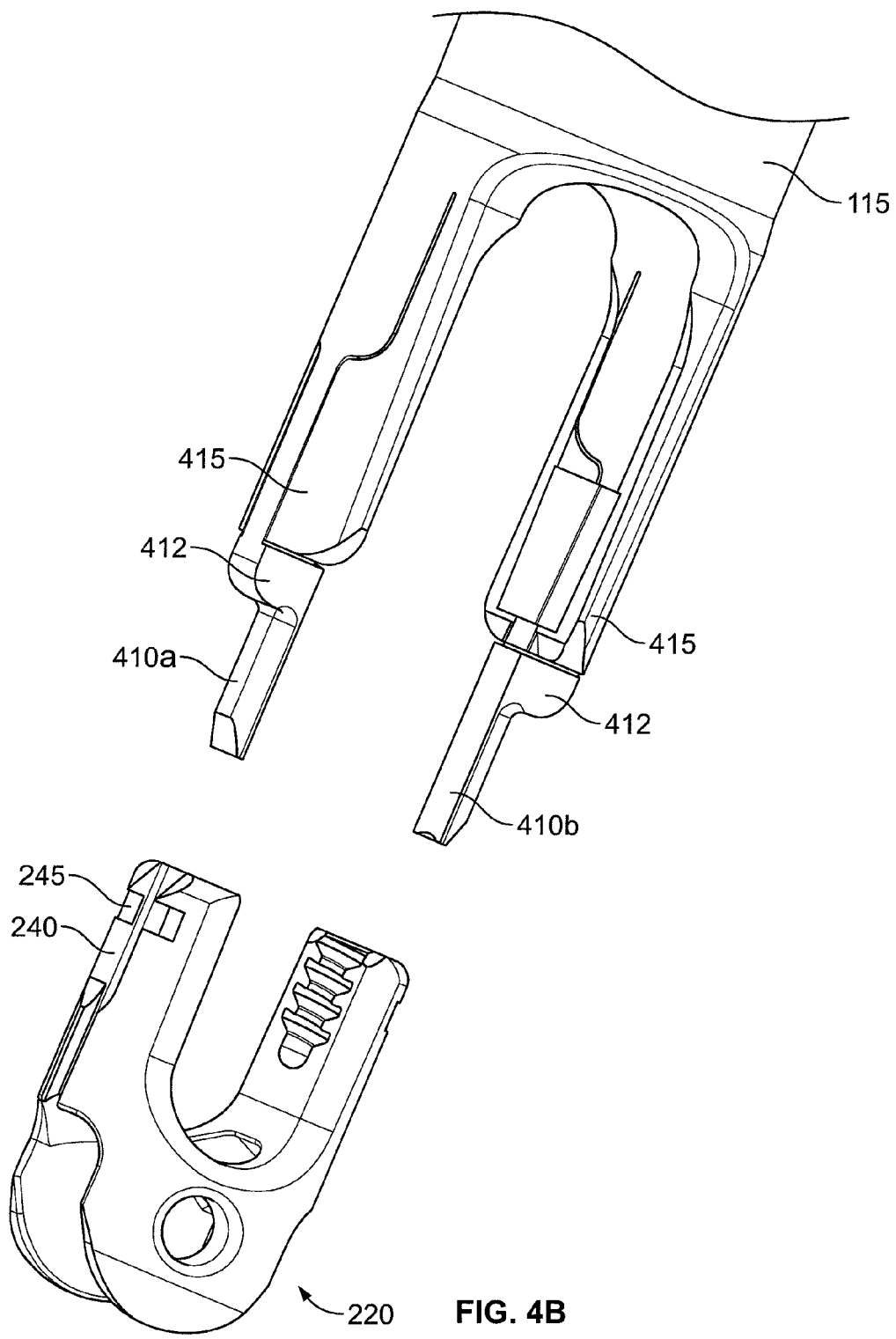
FIG. 4B shows an enlarged view of the distal region of the insertion cannula and the receiver.

The insertion cannula 110 can be securely coupled to the receiver 220 to permit placement and manipulation of the pedicle screw assembly via the insertion cannula 110. As mentioned, a distal region of the insertion cannula 110 can include a pair of opposed prongs 410 that extend distally from the distal end of the insertion cannula 110. The prongs 410 insert and attach to the channels 240 in the receiver 220. The prongs 410 can be associated with the body of the insertion cannula 110 via a relatively broad and stiff base 412 (FIG. 4B). FIG. 4B shows an enlarged view of the distal region of the insertion cannula 110 and the receiver 220. The prongs 410 can be positioned such that they can slide into the channels 240 on the receiver 220. That is, a first prong 410a can be positioned a distance from a second prong 410b such that the first and second prongs 410 can simultaneously slide into first and second channels 240 on the receiver 220.

Figure 4C:
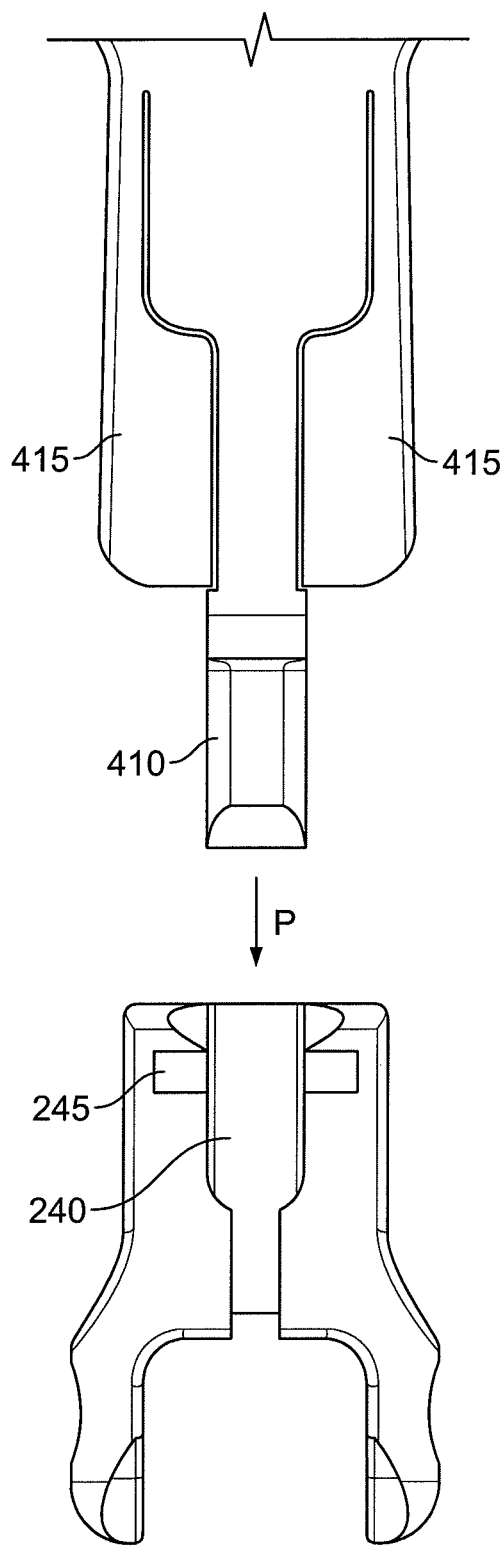
FIGS. 4C and 4D show the insertion cannula being coupled to the receiver.
Figure 4D:
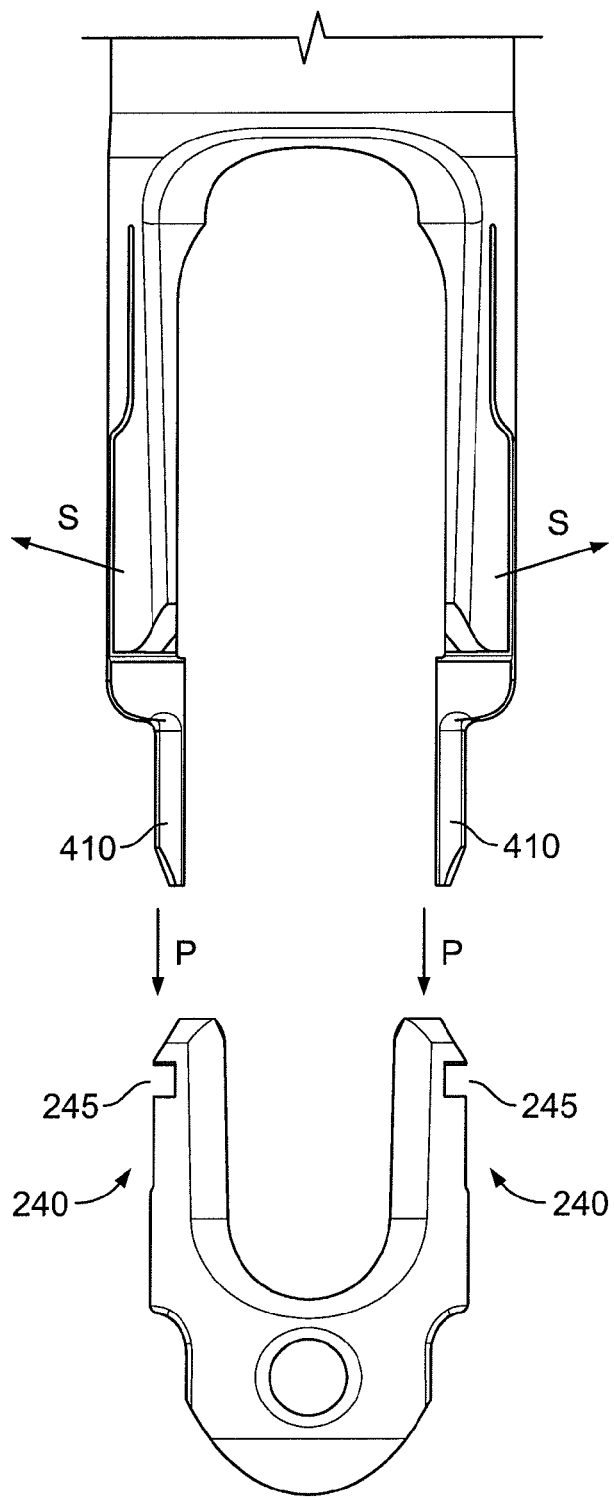

The prongs 410 can slide along a direction parallel to the long axis of the receiver 220 into the confining channels 240 of the receiver 220, as represented by the arrows P in FIGS. 4C and 4D. The channels 240 can include chamfered surfaces 239 that facilitate entry of the prongs 410 into the channels 240. As the prongs 410 slide into the channels 240, a dovetail relationship therebetween prevents the prongs 410 from splaying under high torsional, linear, and angular loads employed during pedicle screw insertion and manipulation, connecting rod association and reduction, as well as set screw insertion and final torquing.

With reference again to FIG. 4B, a set of projecting elements 415 are located on opposed sides of the insertion cannula's 115 distal end. The projecting elements 415 can be located on either side of the prongs 410 such that each prong 410 is interposed between a pair of projecting elements 415. Alternatively, a single projecting element 415 can be positioned adjacent the prong 410 or more than two projecting elements 415 can be positioned adjacent the prong 410. The projecting elements 415 can splay or radially displace outward away from the receiver 220 temporarily as the prongs 410 of the insertion cannula 110 are initially associated into the channels 240 of the receiver 220, as represented by the arrows S in FIG. 4D. The projecting elements 415 can subsequently spring back or passively relax into latched engagement with the slots 245 of the receiver 220. Once the projecting elements 415 are latched with the slots 245, the insertion cannula 110 is fully engaged relative to the receiver element 220. The aforementioned functionality of the projecting elements 415 is accomplished by using a geometry (relatively long, thin, and narrow cantilever) and material (relatively non-ductile and elastic) associated with the projecting elements 415. In addition, locking or grasping undercuts can be associated with the deep surface of the projecting elements 415 and the corresponding superficial surfaces of the receiver 220.

Figure 5A:
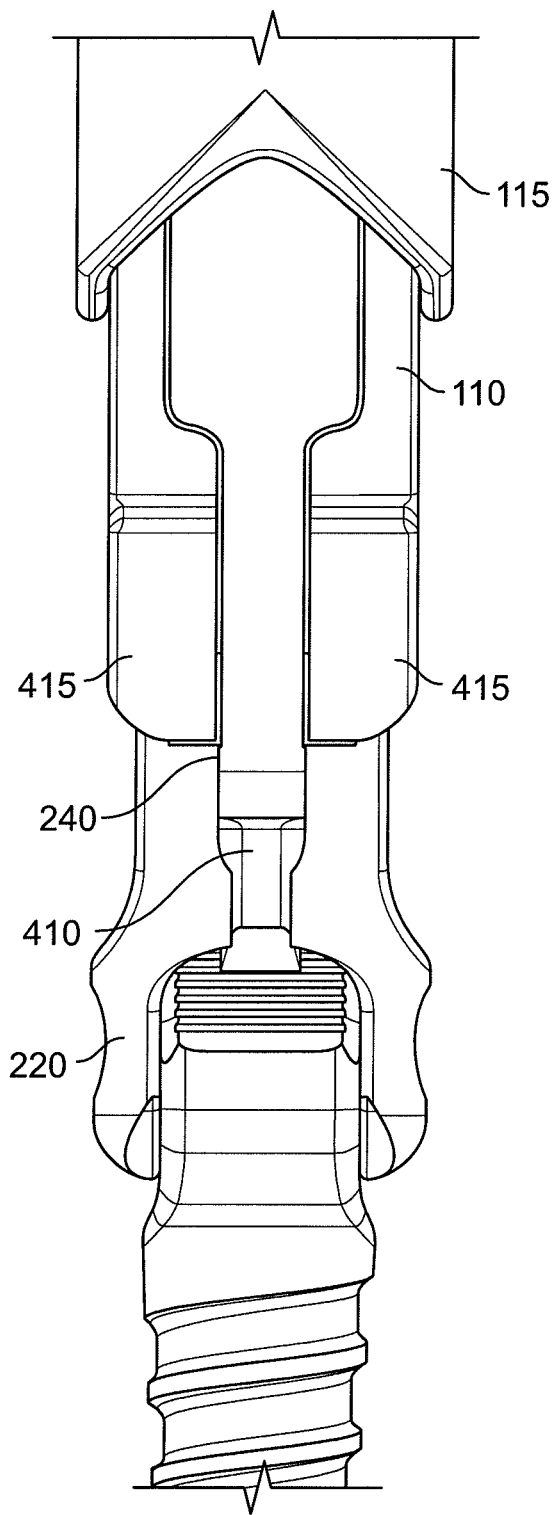
FIGS. 5A and 5B show the insertion cannula fully engaged with the receiver of the pedicle screw assembly.
Figure 5B:
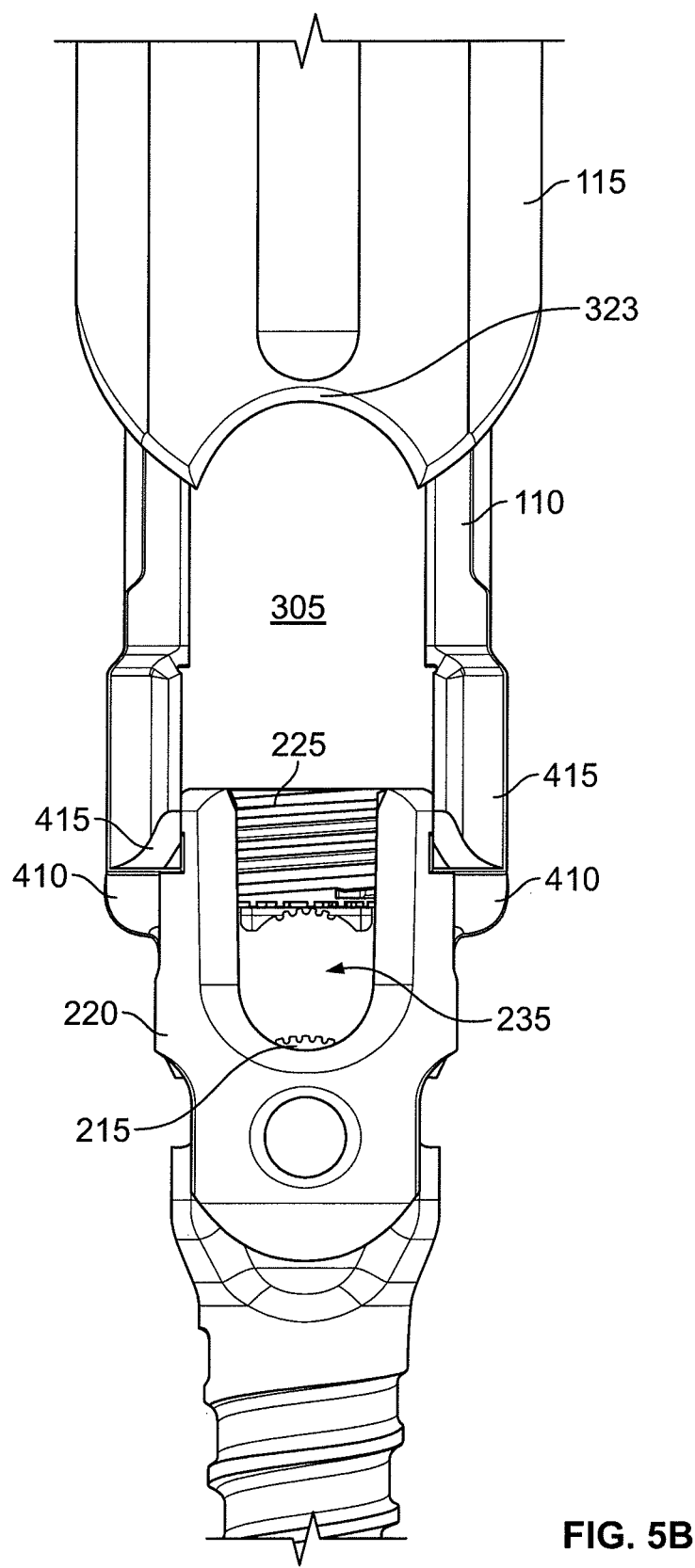

FIGS. 5A and 5B show the insertion cannula 110 fully engaged with the receiver 220 of the pedicle screw assembly 105. The projecting elements 415 are shown latched onto the slots 245 on either side of the receiver 220 with the prongs 410 engaged in a dove-tail relationship with the channels 240 on either side of the receiver 220. This provides a secure and rigid engagement between the insertion cannula 110 and the receiver 220.

As discussed, the cannulae 110, 115 and the receiver 220 define a vaulted opening 305 that facilitates insertion of the rod. FIG. 5B shows the vaulted opening 305, which is defined at an upper or proximal end by the reduction cannula 115 and on a distal or lower end by the receiver 220. The rod (not shown) can be positioned beneath the compression nut 225 during use to permit the compression nut 225 to exert a compression force on the rod. The vaulted opening 305 effectively enlarges or extends the permissible positioning of the connecting rod (well above and slightly wider than the upper limits of the receiver's 220 lateral walls) during connecting rod placement and prior to connecting rod reduction, as well as troughed and/or flat surfaces on either side of the reduction cannula 115 to provide a mechanical and/or tactile facilitation of connecting rod placement (particularly during percutaneous connecting rod insertion). For example, a troughed and/or flat surface markers 315 can be present on the exterior surfaces of the reduction cannula 115 and extending, for example linearly in the caudal and cephalad directions along the long axis of the reduction cannula 115 (see FIG. 3A). A surgeon can use the markers 315 in a tactile manner to locate proper placement of the connecting rod into the opening 305. The projecting tip of the connecting rod (which can be conical or bullet-nosed) can be placed against the reduction cannula 115 and slid into the markers 315 and then deeper into the body until the connecting rod slides distal to the markers 315 and into the opening 305 between the bottom of the insertion/reduction cannulae and the associated receiver 220 of a pedicle screw facilitating "threading" the connecting rod through the receiver 220.

A method of using the insertion-reduction system is now described. The cannula assembly is first coupled to the receiver 220 of the pedicle screw assembly 105. As discussed above, the insertion cannula 110 extending through the internal bore of the reduction cannula 115 is attached to the receiver 220 by sliding the prongs 410 into the channels 240 of the receiver 220. The projecting elements 415 on either side of each prong 410 of the insertion cannula 110 splay outward as the prongs 410 slidingly engage the channels 240. The elements 415 subsequently spring back or relax into latched engagement with the slots 245 of the receiver 220. There is a close approximation of the internal bore 117 of the reduction cannula 115 to the external surface of the insertion cannula's 110 projecting elements 415. The reduction cannula 115 confines the projecting elements 415 and further stabilizes the prongs 410. The relationship between the internal bore 117 of the reduction cannula 115 and the projecting elements 415 prevents dissociation of the receiver 220 from the insertion cannula 110 during the relatively high and otherwise displacing loads experienced with connecting rod reduction and final set screw torquing.

With the pedicle screw assembly 105 attached to the insertion cannula 110, the cannula assembly can be used to manipulate the pedicle screw assembly 105 into a desired position relative to the spine. The connecting rod can then be inserted into the vaulted opening 305 in the receiver 220 above the screw head 215 and below the distal edge of the reduction cannula 115. The reduction cannula 115 is then moved distally toward the screw head 215 while the insertion cannula 110 maintains the pedicle screw assembly 105 in place such that the distal edge of the reduction cannula 115 pushes or reduces the rod toward the screw head 215.

Movement of the reduction cannula 115 relative to the insertion cannula 110 can be achieved by rotating the collar 310 along the threads 405 on the proximal region of the insertion cannula 110. This allows for gradual and forceful linear translation of the reduction cannula 115 distally along the common axis of both cannulas 110, 115 and facilitates reduction of the connecting rod within the receiver's opening 235. The distal most edge 323 of the reduction cannula 115 reduces or pushes the rod distal or downward into the seat of the receiver 220 until the rod is fully reduced. As mentioned, the close approximation of the internal bore 117 of the reduction cannula 115 to the external surface of the insertion cannula's 110 distal projecting elements 415 confines the projecting elements 415 and further stabilizes the prongs 410, thereby preventing dissociation of the pedicle screw receiver 220 from the insertion cannula 110 during the relatively high and otherwise displacing loads experienced with connecting rod reduction and final set screw 225 torquing.

Figure 6:
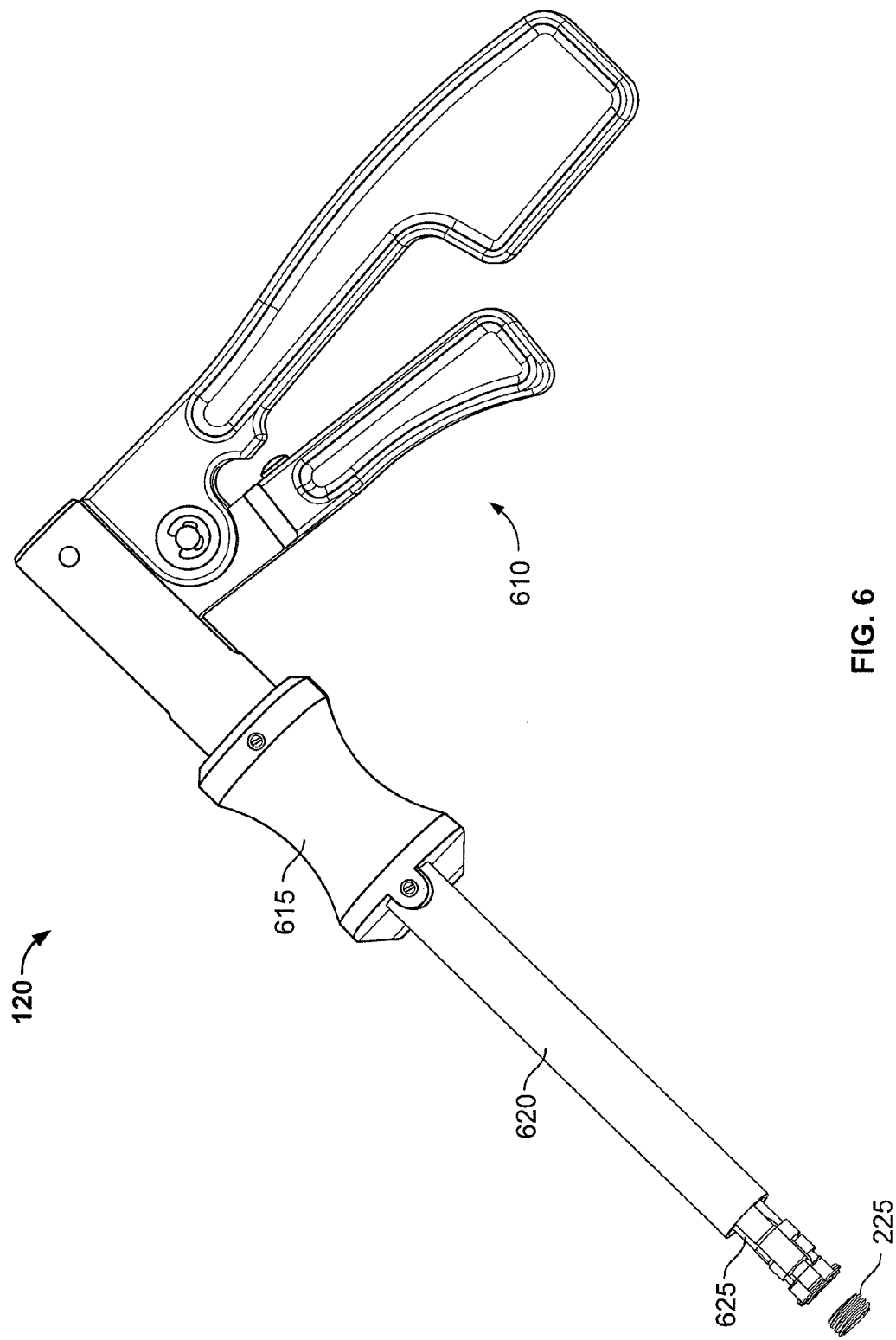
FIG. 6 shows a disengagement tool and a compression nut.

At this stage, the rod is reduced into the receiver 220 of the pedicle screw assembly 105. The tool 120 can then be used to deploy the compression nut 225 onto the receiver 220 over the rod to fixate the rod relative to the pedicle screw assembly 105. FIG. 6 shows the tool 120 and the compression nut 225. The tool 120 includes an actuation handle 610 that can be used to control the tool 120. The tool 120 further includes a coupler 615 that couples the tool 120 to the insertion cannula 110 mounted on the reduction cannula 115 as well as an elongate arm 620 that is sized for insertion into the internal bore 417 of the insertion cannula 110. A distal region of the arm 620 includes a control element 625 that couples with the compression nut 225. The compression nut 225 can be deployed onto the receiver 220 by inserting the arm 620 through the insertion cannula 110 and into engagement with the receiver 220, which is attached the insertion cannula 110.

Figure 7:
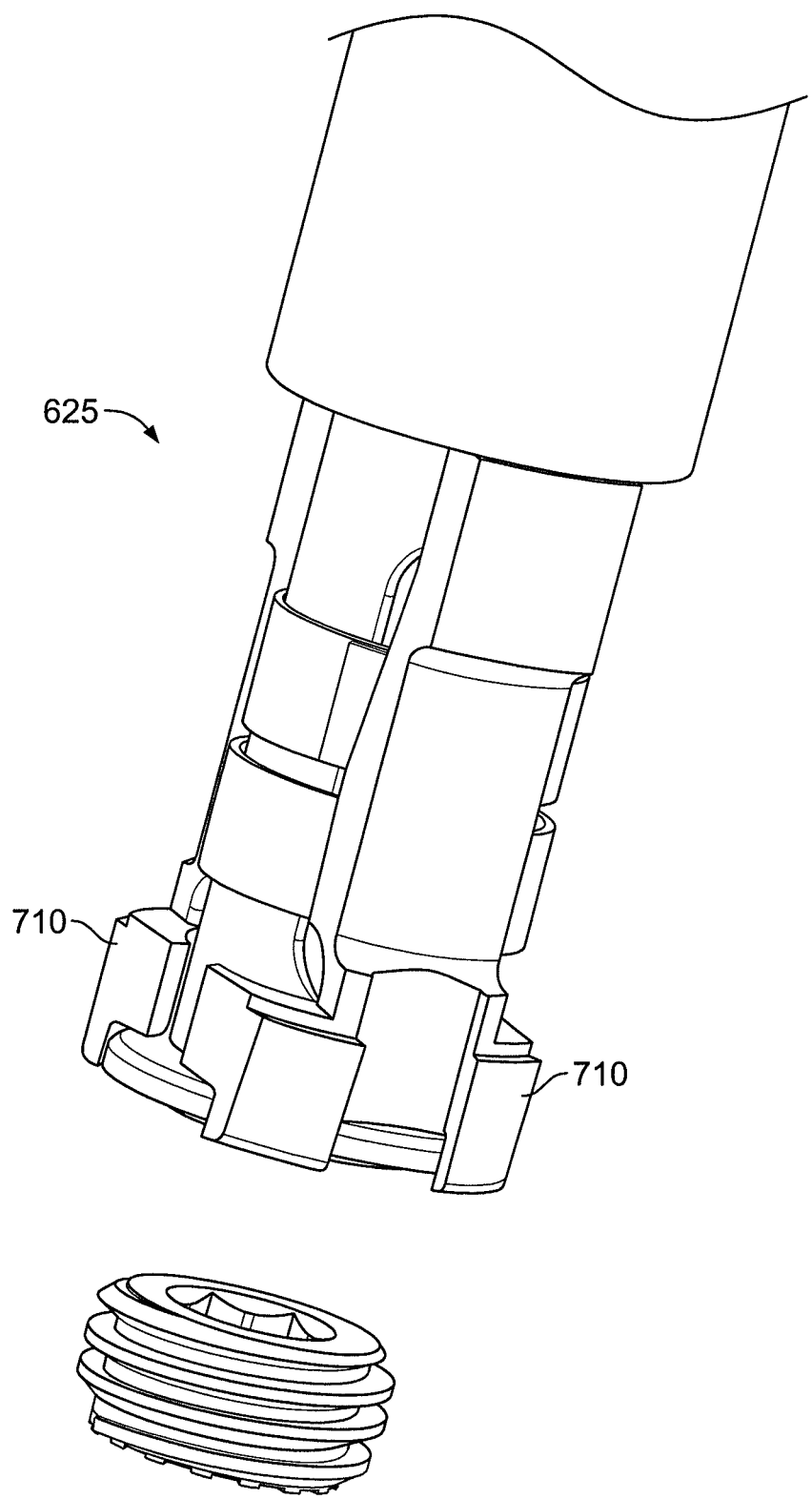
FIG. 7 shows an enlarged view of a control element of the disengagement tool.

The control element 625 also interfaces with the distal region of the insertion cannula 110 to disengage the insertion cannula 110 from the receiver 220 of the pedicle screw assembly 105. FIG. 7 shows an enlarged view of the control element 625 of the tool 120. The control element 625 includes displacing elements 710 that assist in disengagement of the insertion cannula 610 from the receiver 220. The displacing elements 710 sequentially splay the projecting elements 415 radially outward and then push on the upper surface of the set screw, while simultaneously engaging the internal bore 417 of the insertion cannula 110 so as to effectively disengage the insertion cannula 110 from the receiver 220 with minimal pushing or pulling force being applied. This dissociation of the insertion/reduction cannulae from the pedicle screw assembly results in negligible net force applied to the pedicle screw—pedicle interface. The tool 120 also has ball detent feature that secures the cannulae 110, 115 to it after dissociation from the receiver element 220, to prevent or mitigate accidental dropping of the insertion/reduction cannulae with their sharp projecting prongs 410 into the operative field.

Thus, the disclosed cannulae assembly can be used to securely hold and position the pedicle screw assembly via the receiver element for both percutaneous and open surgical applications. The system provides an easy and reliable means for association and dissociation of the insertion and reduction cannulae to the pedicle screw receiver and restricts soft tissue intrusion along the insertion and extraction path of the compression nut used to secure the connecting rod to the pedicle screw assembly. The engagement between the insertion cannula and the receiver provides a means for opposing rotational displacement of the pedicle screw during set screw insertion and final torquing. It also allows for manipulation of the receiver of the pedicle screw relative to the implanted pedicle screw threaded shaft, to facilitate connecting rod association. The cannulae facilitate localization, introduction and reduction of the connecting rod to the pedicle screw receiver element with subsequent ease of set screw application. The cannulae also provide for a means of approximation (compression) and separation (distraction) of adjacent pedicle screws associated with a connecting rod. The aforementioned features can be accomplished with efficient geometry represented by the smallest cross-sectional area and surgical field volume requirements.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

What is claimed is:

1. A method of inserting and reducing a spinal rod into a fixation device assembly, comprising:
    assembling a fixation device assembly comprising a fixation device configured to be engaged with a bone and a rod receiver element having an outer surface comprising a pair of opposed longitudinal channels, each channel intersected cross-wise by a slot;
    coupling a cannula assembly to the receiver element, the cannula assembly comprising:
        a reduction cannula having an internal bore extending between a proximal region and a distal region; and
        an insertion cannula co-axially positioned within the internal bore of the reduction cannula, wherein the insertion cannula comprises a pair of opposed prongs and at least one flexible projecting element extending distally from a distal region of the insertion cannula, wherein the pair of opposed prongs of the insertion cannula and the distal region of the reduction cannula are aligned to collectively define an opening that is sized and shaped for receiving a connecting rod;
    sliding the prongs of the insertion cannula into the longitudinal channels of the receiver element, wherein the flexible projecting element temporarily splays outward and subsequently passively recoils into latched engagement with the slots intersecting the longitudinal channels as the prongs slide into the channels;
    inserting the connecting rod into the opening; and
    moving the reduction cannula distally toward the fixation device while the insertion cannula maintains the fixation device assembly in a desired position.

2. The method of claim 1, wherein the distal region of the reduction cannula has a vaulted leading edge.

3. The method of claim 2, wherein moving the reduction cannula distally comprises pushing the connecting rod into the receiver element with the vaulted leading edge of the reduction cannula.

4. The method of claim 1, wherein moving the reduction cannula comprises rotating an annular collar mounted on the proximal region of the reduction cannula and rotatably coupled to a threaded proximal region of the insertion cannula to impart linear translation between the reduction cannula and the insertion cannula.

5. The method of claim 1, wherein moving the reduction cannula comprises providing gradual and forceful linear translation of the reduction cannula distally along a long axis of the cannula assembly.

6. The method of claim 1, further comprising deploying a compression nut into the receiver element to fixate the connecting rod relative to the fixation device assembly.

7. The method of claim 6, wherein deploying the compression nut comprises using a tool comprising: an actuation handle; a cannula assembly coupler element configured to couple the tool to the cannula assembly; and an elongate arm comprising a distal control element.

8. The method of claim 7, wherein the distal control element comprises an opening configured to receive and hold the compression nut.

9. The method of claim 7, wherein using the tool comprises inserting the elongate arm through an internal bore of the insertion cannula.

10. The method of claim 9, further comprising using the distal control element of the tool to sequentially splay the projecting element radially outward and push downward on an upper surface of the compression nut while simultaneously engaging the internal bore of the insertion cannula to disengage the insertion cannula from the receiver element.

11. The method of claim 10, wherein using the tool to disengage the insertion cannula from the receiver element applies negligible net force to the receiver element.

* * * * *